(12) United States Patent
Ironside

(10) Patent No.: US 11,842,492 B2
(45) Date of Patent: Dec. 12, 2023

(54) CEREBRAL HEMATOMA VOLUME ANALYSIS

(71) Applicant: Natasha Ironside, Charlottesville, VA (US)

(72) Inventor: Natasha Ironside, Charlottesville, VA (US)

(*) Notice: Subject to any disclaimer, the term of this patent is extended or adjusted under 35 U.S.C. 154(b) by 0 days.

(21) Appl. No.: 17/959,438

(22) Filed: Oct. 4, 2022

(65) Prior Publication Data

US 2023/0078532 A1    Mar. 16, 2023

Related U.S. Application Data

(63) Continuation-in-part of application No. 17/724,395, filed on Apr. 19, 2022.

(60) Provisional application No. 63/176,519, filed on Apr. 19, 2021.

(51) Int. Cl.
*G06K 9/00* (2022.01)
*G06T 7/00* (2017.01)
*G16H 20/00* (2018.01)

(52) U.S. Cl.
CPC ........... *G06T 7/0014* (2013.01); *G16H 20/00* (2018.01); *G06T 2207/10081* (2013.01); *G06T 2207/20084* (2013.01); *G06T 2207/30016* (2013.01)

(58) Field of Classification Search
CPC . G06T 2207/30016; G06T 2207/20081; G06T 2207/20084; G06T 2207/10081; G06T 2207/10072–10112; G06K 9/6256; G06K 9/6257; G06K 9/6259; G06V 10/70; G06V 10/82; G06V 10/774–7796; G06N 3/02–126; G06N 20/00–20
See application file for complete search history.

(56) References Cited

U.S. PATENT DOCUMENTS

| | | | |
|---|---|---|---|
| 7,676,257 B2 | 3/2010 | Suryanarayanan et al. | |
| 9,165,360 B1 | 10/2015 | Bates et al. | |
| 9,723,988 B2 | 8/2017 | Kakimoto et al. | |
| 10,282,663 B2 | 5/2019 | Socher et al. | |
| 2010/0260394 A1 | 10/2010 | Meetz et al. | |
| 2012/0114205 A1 | 5/2012 | Tang et al. | |
| 2016/0210742 A1 | 7/2016 | Weiss | |
| 2016/0292864 A1 | 10/2016 | Dabbah et al. | |
| 2018/0144467 A1* | 5/2018 | Sofka ................... G01R 33/445 | |

(Continued)

OTHER PUBLICATIONS

Natasha Ironside: "Fully Automated Segmentation Algorithm for Hematoma Volumetric Analysis in Spontaneous Intracerebral Hemorrhage" Stroke. 2019;50:3416-3423. DOI: 10.1161/STROKEAHA.119.026561.

(Continued)

*Primary Examiner* — Atiba O Fitzpatrick
(74) *Attorney, Agent, or Firm* — Millen, White, Zelano & Branigan, P.C.; William F. Nixon

(57) ABSTRACT

A system performs cerebral hematoma analysis. The system includes a computing device receiving computerized tomography (CT) images from CT imaging devices. The CT images are associated with patients exhibiting cerebral hematomas. CT images may be converted into feature vectors and passed as input to a convolution neural network model for identification and diagnosis of hematoma volume changes. Detected changes may be thresholded to determine if the change represents an increase or shrinkage in the volumetry of the hematoma.

17 Claims, 7 Drawing Sheets

(56) References Cited

U.S. PATENT DOCUMENTS

| | | |
|---|---|---|
| 2018/0365824 A1 | 12/2018 | Yuh et al. |
| 2019/0019304 A1* | 1/2019 | Takei et al. |
| 2019/0021677 A1* | 1/2019 | Grbic .................... G06T 7/11 |
| 2020/0090331 A1* | 3/2020 | Mansi ................ A61B 5/4064 |
| 2020/0357120 A1* | 11/2020 | Kang .................. A61B 5/0042 |
| 2020/0411173 A1* | 12/2020 | Mansi .................. G16H 15/00 |
| 2021/0020304 A1* | 1/2021 | Bakhshinejad ....... G06T 7/0014 |
| 2021/0174939 A1* | 6/2021 | Huang ................. A61B 6/032 |
| 2022/0309667 A1* | 9/2022 | Yoo ..................... G06T 7/0016 |

OTHER PUBLICATIONS

Natasha Ironside:"Fully Automated Segmentation Algorithm for Perihematomal Edema Volumetry After Spontaneous Intracerebral Hemorrhage" Stroke. 2020;51:815-823. DOI: 10.1161/STROKEAHA.119.026764.

* cited by examiner

|  | Fully Automated vs Manual | Fully Automated vs Semi-automated |
|---|---|---|
| Mean volumetric DC±SD | 0.894±0.264 | 0.905±0.254 |
| Mean Haussdorf distance, mm±SD | 218.84±335.83 | 277.69±368.04 |
| Mean surface distance, mm±SD | 5.19±23.65 | 5.09±16.47 |
| Mean relative absolute volume difference, %±SD | 17.97±14.55 | 16.18±14.19 |

DC indicates Dice coefficient

FIG. 6A   FIG. 6B   FIG. 6C   FIG. 6D

| Outcome | Manual | Semi-automated | Fully Automated | df | F Statistic | P Value |
|---|---|---|---|---|---|---|
| ICH volume, mean mL ± SD* | 25.73 ± 23.72 | 26.54 ± 25.24 | 25.60 ± 25.99 | 2, 117 | 0.09 | 0.915 |
| Volumetric analysis time, mean seconds ± SD* | 201.45 ± 92.22 | 288.58 ± 160.32 | 11.97 ± 2.70 | 2, 117 | 639.01 | <0.0001† |

FIG. 7

| Pairwise Comparisons | Fully Automated vs Manual | P Value† | Fully Automated vs Semi-automated | P Value† | Semi-automated vs Manual | P Value† |
|---|---|---|---|---|---|---|
| Difference in ICH volume, mean mL [95% CI] | -0.13 [-13.36 to 13.10] | 0.954 | -0.94 [-14.17 to 12.29] | 0.912 | 0.809 [-12.42 to 14.04] | 0.993 |
| Difference in volumetric analysis time, mean seconds [95% CI] | -189.48 [-246.17 to -132.79] | <0.0001* | -276.61 [-333.30 to -219.92] | <0.0001* | 87.13 [30.44 to 143.81] | 0.002* |

FIG. 8

CEREBRAL HEMATOMA VOLUME ANALYSIS

CROSS-REFERENCE TO RELATED APPLICATIONS

This application claims the benefit of priority under 35 U.S.C. 120 to provisional patent application No. 63/176,519 entitled "Fully Automated Segmentation Algorithm for Hematoma Volumetric Analysis for Spontaneous Intracerebral Hemorrhage" filed on Apr. 19, 2021 and provisional patent application No. 63/176,777 entitled "Fully Automated Segmentation Algorithm for Perihematomal Edema Volumetry after Spontaneous Intracerebral Hemorrhage" filed on Apr. 19, 2021.

CEREBRAL HEMATOMA VOLUME ANALYSIS

The technical subject matter of this application relates generally to the field of patient condition diagnostics using medical image analysis. Specifically, the claimed subject matter relates to detecting changes in the volume of a cerebral hematoma.

BACKGROUND

Cerebral bleeding is a serious health problem affecting many people throughout their lifetime. Spontaneous cerebral bleeding occurs unpredictably or without warning. Various diseases can increase the risk of spontaneous cerebral hemorrhage including high blood pressure, blood clotting disorders and diabetes. Bleeding of the brain is particularly common in older individuals. Unlike surface or on-the-skin bleeding, internal bleeding within the cranial cavity can be difficult to detect and monitor. Medical imaging by specialized equipment is required in order to locate and visualize the bleeding; and further imaging is required in order to detect changes in hemorrhage patterns.

Current techniques for identifying brain bleeding use magnetic resonance imaging (MRI), computerized tomography (CT), or other types of scan technology to capture images of the cranial cavity. Physicians then review the captured images to determine whether there is evidence of a cerebral hemorrhage. By repeating this process over time, physicians can detect changes in the volume of a brain hemorrhage that could mean increased or reduced bleeding and signs of changes to the underlying clinical state of the affected patient.

SUMMARY

Various embodiments are directed to a system for cerebral hematoma analysis. The analysis of CT images by an artificial intelligence model may increase the speed, efficiency and reliability of hematoma change identification. This in turn reduces diagnostic time and may improve patient outcomes.

One embodiment of the invention is a computing device including a processor, a display, a network communication interface, and a computer readable medium, coupled to the processor, the computer-readable medium comprising code, executable by the processor. The code may cause the processor to implement the steps of receiving, from a computerized tomography (CT) imaging device, a CT image of a patient exhibiting ICH and separating the CT image into CT image slices. The code may also include instructions for converting each CT image slice into a feature vector and passing the feature vectors to a convolutional neural network (CNN) model as input; then executing the CNN model to obtain an estimate of ICH volumetry. The estimate may be compared to a threshold, and based on the results of this comparison, determine a change in the medical status of the patient's ICH volume.

Additional embodiments include methods and processor-executable code stored on non-transitory computer-readable media for cerebral hematoma analysis. Systems for implementing these are also contemplated as embodiments.

Additional details regarding the specific implementation of these embodiments can be found in the Detailed Description and the Figures.

BRIEF DESCRIPTION OF THE DRAWINGS

FIG. 6 shows a comparison of CT image segmentations grouped by segmentation method according to various embodiments.

FIG. 7 shows a table illustrating a comparison of performance parameters across CT image segmentation methods according to an embodiment.

FIG. 8 shows a table illustrating a comparison of data set parameters across CT image segmentation methods according to an embodiment.

DETAILED DESCRIPTION

Figure 1:
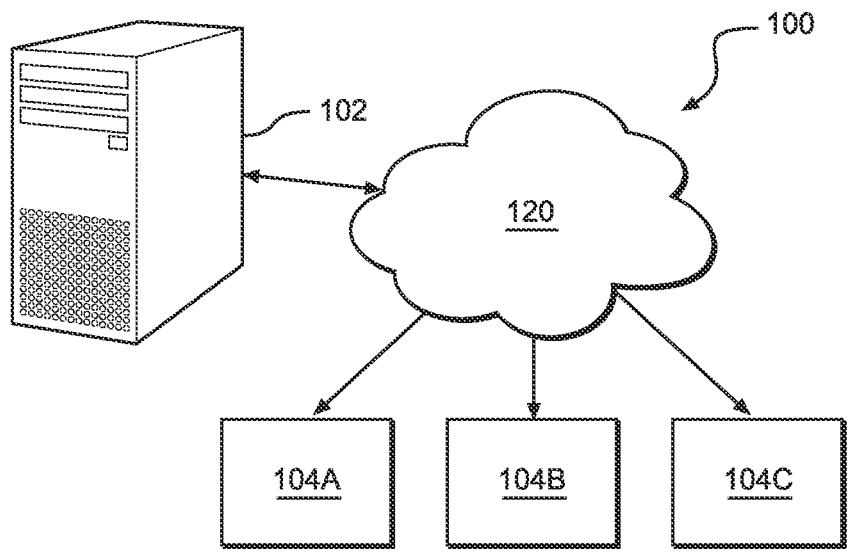
FIG. 1 shows a block diagram of a computing system environment suitable for implementing an intracerebral hematoma volumetric analysis system according to various embodiments.

Reference will now be made in detail to specific embodiments of the present invention. Examples of these embodiments are illustrated in the accompanying drawings. Numerous specific details are set forth in order to provide a thorough understanding of the present invention. While the embodiments will be described in conjunction with the drawings, it will be understood that the following description is not intended to limit the present invention to any one embodiment. On the contrary, the following description is intended to cover alternatives, modifications, and equivalents as may be included within the spirit and scope of the appended claims. Numerous specific details are set forth in order to provide a thorough understanding of the present invention.

Prior to discussing embodiments of the invention, some terms can be described in further detail.

A "computing device" may be a computing device that executes an application for artificial intelligence model building and use in diagnosing cerebral hematoma changes. A computing device may receive images from medical imaging devices with which it is in direct or networked communication. The computing device may maintain one or more data stores of image data, models, and software applications. This device may be a server, servers, workstations, personal computers (PC), tablets, and the like.

A "display" may be any electronic output device that displays or renders data in a pictorial or textual format. Displays may include computing device monitors, touch-screen displays, projectors, and the like.

A "CT imaging device" or "medical imaging device" may be a computerized tomography imaging device. The CT imaging device may be any device capable of using sensors to scan a portion of a patient's body and output CT image stacks of the sensor-collected data.

A "network communication interface" may be an electrical component that enables communication between two computing devices. A network communication interface may enable communications according to one or more standards such as 802.11, BlueTooth, GPRS, GSM, 3G, 4G, 5G, Ethernet, or the like. The network communications interface may perform signal modulation/demodulation. The network communications interface may include digital signal processing (DSP). Some embodiments may include computing devices that include multiple communications interfaces to enable communications according to different protocols or standards.

An "Electronic message" refers to an electronic message for self-contained digital communication that is designed to be transmitted between physical computing devices. Electronic messages may include but are not limited to transmission control protocol (TCP) messages, user datagram protocol (UDP) message, electronic mail, a text message, an instant message, transmit data, or a command or request to access an Internet site.

A "user" may include an individual or a computational device. In some embodiments, a user may be associated with one or more individual user accounts and/or mobile devices or personal computing devices. In some embodiments, the user may be an employee, contractor, or other person having authorized access to make use of a networked computing environment.

A "server computing device" is typically a powerful computer or cluster of computers. For example, the server computer can be a large mainframe, a minicomputer cluster, or a group of servers functioning as a unit. In one example, the server computer may be a database server and may be coupled to a Web server. The server computing device may also be referred to as a server computer or server.

A "processor" may include any suitable data computation device or devices. A processor may comprise one or more microprocessors working together to accomplish a desired function. The processor may include CPU or GPU comprising at least one high-speed data processor adequate to execute program components for executing user and/or system-generated requests. The CPU may be a microprocessor such as AMD's Athlon, Duron and/or Opteron; IBM and/or Motorola's PowerPC; IBM's and Sony's Cell processor; Intel's Celeron, Itanium, Pentium, Xeon, and/or XScale; and/or the like processor(s).

A "memory" may be any suitable computer-readable device or devices that can store electronic data. A suitable memory may comprise a non-transitory computer readable medium that stores instructions that can be executed by a processor to implement a desired method. Examples of memories may comprise one or more memory chips, disk drives, removable memory, etc. Such memories may operate using any suitable electrical, optical, and/or magnetic mode of operation.

Various methods and techniques described herein provide solutions for detecting changes in the size of cerebral hemorrhage (i.e., brain bleeding). Embodiments provide for the generation of one or more machine learning models that analyze computerized tomography (CT) scans of the cranial cavity of patients diagnosed with particular forms of cerebral hemorrhage. The output of the model(s) may provide estimates of the change in the volume, shape, and, or density of a patient hematoma across CT images. Diagnostic recommendations may be made based, at least in part, on the identified changes. These techniques may improve the speed, accuracy and precision of diagnosing cerebral hemorrhage changes to enable health care providers to more quickly and appropriately administer care interventions.

Spontaneous intracerebral hemorrhage (ICH) affects approximately 15 to 25 per 100,000 persons worldwide. It is associated with high rates of mortality and functional disability. The prognosis and treatment decisions for ICH patients are most strongly influenced by initial hematoma volume and subsequent change in hematoma volume, both of which are used as surrogate markers for patient outcome to represent the underlying clinical condition of the patient. Initial hematoma volume and interval stability are eligibility criteria to determine which patients are the most optimal candidates for intervention. Timely identification of the initial ICH volume and a change in that volume improves the likelihood that early intervention is performed on appropriate patients to positively affect patient outcomes.

Non-contrast CT is the most commonly used neuroimaging modality for serial hematoma assessment in ICH patients, due to its cost-effectiveness, pervasive availability and rapid image acquisition. Accurate edge-detection is important to the identification of changes in the volume of ICH. Semi-automated ICH edge-detection methods are both time consuming and fraught with substantial measurement error, especially for large hematomas associated with intraventricular hemorrhage (IVH) and/or subarachnoid hemorrhage (SAH). Manual ICH edge-detection methods are even more time consuming and have a high inter-user variability. The accuracy of semi-automated and manual ICH edge-detection methods also depend on the expertise of the rater; and the generalizability of these various measurement techniques has been constrained by their inefficiencies.

The various embodiments provide solutions to the above-referenced challenges in edge-detection for identifying volume changes in cerebral hematomas. The disclosed embodiments employ convolutional neural networks (CNN) for CT image analysis to overcome the limitations of currently available CT-based cerebral hematoma identification and volume analysis methods. The various embodiments include computing devices, and systems, executing a method of generating and using a CNN model for fully automated cerebral hematoma volumetry from CT scans of patients with ICH.

For simplicity of illustration, a certain number of components are shown in FIG. 1. It is understood, however, that embodiments of the invention may include more than one of each component. In addition, some embodiments of the invention may include fewer than or greater than all of the components shown in FIG. 1.

I. The Analysis Environment

FIG. 1 illustrates an exemplary computing system 100 for intracerebral hematoma volumetric analysis according to various embodiments. With reference to FIG. 1, a system 100 may generate a CNN model based on the CT image scans of the cranial cavity of multiple patients. The CT images may be collected from patients via one or more CT imaging devices 104A, 1048, 104C and communicated or transmitted to a computing device 102 via a connection that is either direct or over a network 120. Image data may be stored in a data store accessible by the computing device 102. The collected CT images ae used to train a CNN model to identify changes in the volume, shape, and, or density of ICH regions within patient images. The trained CNN model is then used by computing device 102 or other devices within the system 100 to diagnose ICH changes and recommend care interventions.

The system 100 includes one or more CT imaging devices 104A-C in communication with a computing device 102 capable of performing image segmentation, model training, model testing, and model use in diagnosing ICH region changes within CT images. Each of the CT imaging devices 104A-C is configured to perform CT imaging on a portion of a patient located within a scanning area such as within an enclosed region of the CT imaging device. The result of performing CT scanning of a portion of a patient is a CT image data file. The CT scan data is interpreted and converted to CT image data by CT imaging software applications local to the CT imaging device 104A-C or a control terminal connected thereto. Resulting CT image data includes multiple image slices, i.e. individual images. Either one or both of the CT scan data and CT image data may be stored locally for a temporary period of time, or transmitted immediately to the computing device 102.

The system 100 may be a part of a broader research or healthcare computing environment and may connect any number of computing devices such as computing device 102 to various computing systems throughout the broader Organization via a network 120. The CT image analysis system 100 can include any suitable network infrastructure including servers, data stores (i.e., databases), computing devices, mobile communication devices, etc. Data generated by other computing systems of the Organization may be transferred and/or transmitted to the computing device 102 by one or more infrastructure components. As illustrated in FIG. 1, CT imaging devices 104A-C, which may be associated with different organizational units (e.g., different wings of a hospital), may transmit data related to CT imaging to the computing device 102 via the network 120.

The system 100 includes a networked environment in which the computing device 102 is connected to the CT imaging devices 104A-C via a network 120. The network 120 enables the transmission of data such as CT image data to various computing devices throughout the networked environment. In some embodiments, the data may be stored in a network server or database (not shown) that is accessed via computing device 102. In other embodiments, the computing device 102 may be directly connected or in direct communication with the CT imaging device 104A. This may include the transmission of data from the CT imaging device 104A to the computing device 102 over a wired communications port and connected cable.

The computing device 102 includes a combination of software, data storage, and processing hardware that enable it to receive, manipulate, and convert medical image data; and use the image data to train and test a CNN model for diagnosing changes in intracerebral hematoma volumes. CT image data or an image stack derived therefrom is transmitted by imaging devices 104A-C over network 120 for collection and aggregation by computing device 102, which may organize and store the data in a data store. The CT image data may be aggregated until CT images from a threshold number of patients have been received from the CT imaging devices 104A-C and stored in the data store. A portion of the aggregated CT images are then used to train a CNN model to identify changes in the volumetry of ICH volumes illustrated in the CT images for a patient.

The data store may be any suitable data storage in operative communication with the computing device 102. For example, the data store may be stored in a memory of the computing device 102 or in one or more external databases. Location of the data store within system 100 is fungible, such that the data store may sit within any system of a broader healthcare or research Organization, so long as it is in communication with computing device 102. The data store may retain data generated, modified, or otherwise published by various systems of the Organization as part of CNN model generation, training, or subsequent CT image analysis completion. The data store may also store models, analysis scripts, or other frequently used software code used to perform analysis of the CT images obtained by CT imaging devices 104A-C.

The computing device 102 may employ multiple software modules including programming code instructing a processor of the computing device to analyze CT image data received from the various CT imaging devices 104A-C. One or more CNN models may be generated and stored as part of a software application executing on the computing device 102, to enable quick and accurate analysis of image stacks derived from CT image data. Administrators may access the CNN model and perform CT image data analysis via a diagnostics application. Using the diagnostics application, administrators may create templates or scripts to expedite use of the CNN model for CT image data analysis. Executing data analysis using the templates or scripts may cause the processor of the computing device 102 to execute the CNN model in the same processing session without additional instructions from an administrator.

Personnel operating the CT imaging devices 104A-C complete CT imaging of patients to obtain CT scan data. During completion of a CT imaging session, physical and, or logical components of a CT imaging device 104A-C are accessed by personnel to take required action. For example, the action may include use of CT imaging sensors to generate CT scan data files, as well as the modification of files, generation of structured or unstructured data, and, or modification of structured or unstructured data. That is, the use of CT imaging sensors of the CT imaging devices 104A-C to scan portions of a patient body may result in the generation of various forms of CT scan data that is converted into CT image data. The CT image data may include image data, meta data, system data, and the like.

Software modules executing on the computing device 102 may separate aggregated CT image data and associated image stacks into test data and training data sets for use in generating a CNN model. The set of training data is used by a model training software module to train a CNN model to identify regions of an ICH region within an image, and the subsequent changes to the ICH region between CT images obtained during different CT imaging sessions. The set of training data is provided as input to the CNN model and the output is compared against manual measurements of ICH region changes. In this manner, the accuracy of the CNN model is checked before its deployment within the system 100 for live image analysis.

Applying the CNN model to CT image data results in the identification of a measurement of change in ICH image characteristics between CT image sessions. Changes in ICH image characteristics include changes in the size of structure as determined by the number of pixels representing ICH, changes in the age of the structure as determined by the density of the pixels representing ICH and changes in the shape of the structure as determined by the boundary or border of the pixels representing ICH. Identification of these changes between CT imaging sessions may indicate changes to the volume of the underlying hematoma and its effects on surrounding brain tissue. CT image data from multiple CT imaging sessions may be used as input to the CNN model and the resultant measurements of difference stored in the data store. For example, an anonymized identifier of the patient may be assigned during initial CT image capture, and all subsequent CT images and the CT image analysis results may be stored in database fields associated with the patient identifier. Reports or summaries of CNN model results may be generated by the computing device 102 and transmitted to any requesting parties, or stored in the data store for later use. In this manner, the results of the CNN model may be used to track changes over time of ICH volumes within a patient, and enable caregivers to diagnose changes to that patient's medical condition.

Figure 2:
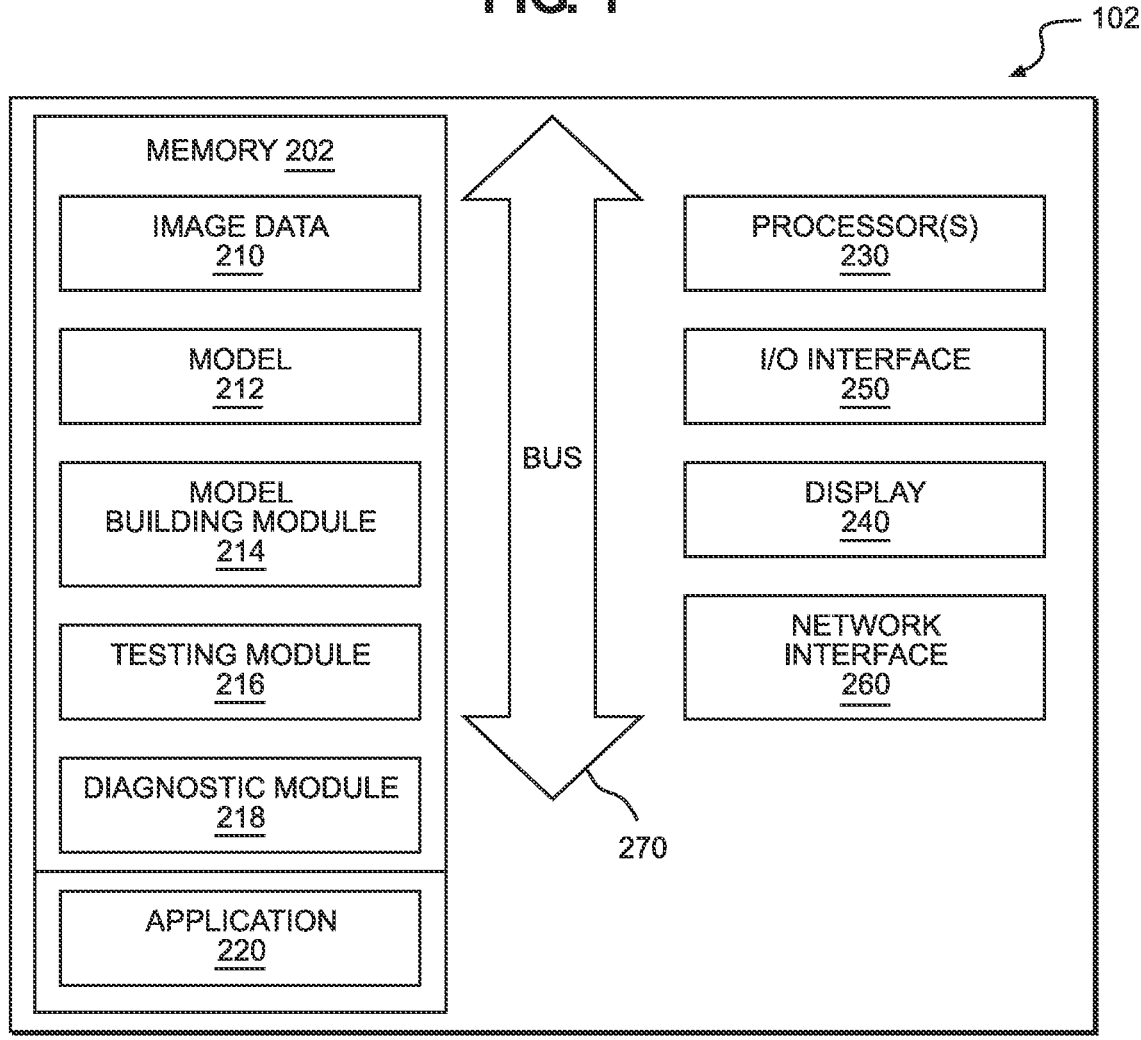
FIG. 2 shows a block diagram of a computing device according to various embodiments.

Referring now to FIG. 2, there is shown an example of a computing device 102 within which a set of instructions, used by the computing system to perform any one or more of the methods discussed herein, may be executed. With reference to FIGS. 1-2, the computing device 102 may receive and analyze CT images from CT imaging devices 104A-C. In some implementations, the computing device 102 may create and execute a CNN model for analyzing CT images of ICH volumes, thus enabling the detection of changes to a patient's medical status with regard to the ICH volume.

In certain implementations, the computing device 102 may be connected (e.g., via a network, such as a Local Area Network (LAN), an intranet, an extranet, or the Internet) to other computer systems. The computing device 102 may operate in the capacity of server or a client computer in a client-server environment, or as a peer computer in a peer-to-peer or distributed network environment. Computing device 102 may be provided by a personal computer (PC), a tablet PC, a set-top box (STB), a Personal Digital Assistant (PDA), a cellular telephone, a web appliance, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein for generating and executing a CNN model for identifying changes in ICH region via CT image analysis.

The computing device 102 includes a processing device such as a processor(s) 230, a memory 202 which includes multiples: a main memory (e.g., read-only memory (ROM), flash memory, dynamic random access memory (DRAM) (such as synchronous DRAM (SDRAM) or DRAM (RDRAM), etc.) and a static memory (e.g., flash memory; a static random access memory (SRAM), etc.), and a data storage device (e.g. data store), which communicate with each other via a bus 270.

Processor 230 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processor 230 may also be one or more special-purpose processing devices such as an application specific integrated circuit (ASIC), a field programmable gate array (FPGA), a digital signal processor (DSP), graphics processing unit (GPU), network processor, or the like. The processor 230 is configured to execute processing logic for performing the operations and steps discussed herein.

The computing device 102 may further include a network communication interface 260 communicably coupled to a network 110. The computing device 102 also may include a video display unit such as display 240 (e.g., a liquid crystal display (LCD) or a cathode ray tube (CRT)), an input/output interface 250 including an alphanumeric input device (e.g., a keyboard) and, or a cursor control device (e.g., a mouse), and an optional signal generation device (e.g., a speaker).

The memory 202 may include a computer-readable storage medium (e.g., a non-transitory computer-readable storage medium) on which may store instructions encoding any one or more of the methods or functions described herein, including instructions encoding applications 220 and modules 214, 216, and 218 for receiving CT image data, converting the CT image data into image stacks, sorting the data into testing and training sets, generating a CNN model to identify changes in ICH region from a CT image data input, and using the output of the CNN model CT image analysis to diagnose changes in ICH region and a patient's underlying medical status, which may also reside, completely or partially, within volatile memory and/or within processor(s) 230 during execution thereof by computing device 102, hence, volatile memory of memory 202 and processor(s) 230 may also constitute machine-readable storage media.

The non-transitory machine-readable storage medium may also be used to store instructions to implement applications 220 for supporting the receiving of CT image data, the building of a CNN model 212, and the use of that model to diagnose changes in ICH volumes within CT images of a patient. While the machine-accessible storage medium is shown in an example implementation to be a single medium included within memory 202, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that is capable of storing, encoding or carrying a set of instructions for execution by the machine and that causes the machine to perform any one or more of the methodologies of the disclosure. The term "machine-accessible storage medium" shall accordingly be taken to include, but not be limited to, solid-state memories, and optical and magnetic media.

One or more modules of processor-executable instructions may be stored in the memory 202 performing various routines and sub-routines of the methods described herein. For example, the model building module 214 may include instructions for executing the receiving of data from CT imaging devices 104AC, the formation of a training data set from the image data 210, and the use of that training data to build a CNN model 212 for analyzing CT images by the computing device 102. The testing module 216 may provide instructions for testing the CNN model 212 using a testing data set, which is a sample of the image data 210.

In various embodiments, the computing device 102 may also include diagnostic module 218 for diagnosing a change in medical status based on an identified change in the volume, shape, or density of an ICH region within a patient. For example, the output of the CNN model may be a measurement of difference in pixels, between two CT images including an ICH region of a patient. This measurement may be positive or negative indicating growth or reduction on volumetry respectively. The measurement of difference may be compared to one or more thresholds to detect if the change is significant. That is, whether the change indicates a change in the patient's underlying medical status, such as expansion of an ICH region that indicates further bleeding in the cranial cavity, or a reduction in volumetry which may indicate healing of the injury and absorption of the blood.

The software applications 220 may provide additional functionality associated with the receipt and manipulation of CT data, as well as the storage and access of data within the data store. Applications 220 may enable the conversion of CT image data into DICOM images. The applications 220 may also assist in the addition, search, and manipulation of data to data store. That is, the applications 220 may provide support functionality for the model building module 214, the testing module 216, and the diagnostic module 218.

II. The Data Set

Various embodiments include the generation and testing of a CNN model using CT images in which an ICH region is presented. In order to generate the CNN model, a data set of CT images of patients known to be experiencing spontaneous ICH must be curated. The data set consists of images of patients confirmed to have spontaneous ICH; the images having been reviewed and rated using one or more manual or semi-automated methods to segment and tag the ICH regions within the slices of CT images. Segmentation and tagging of the CT images in preparation for CNN model generation may including multiple phases to reduce noise and error.

Figure 3:
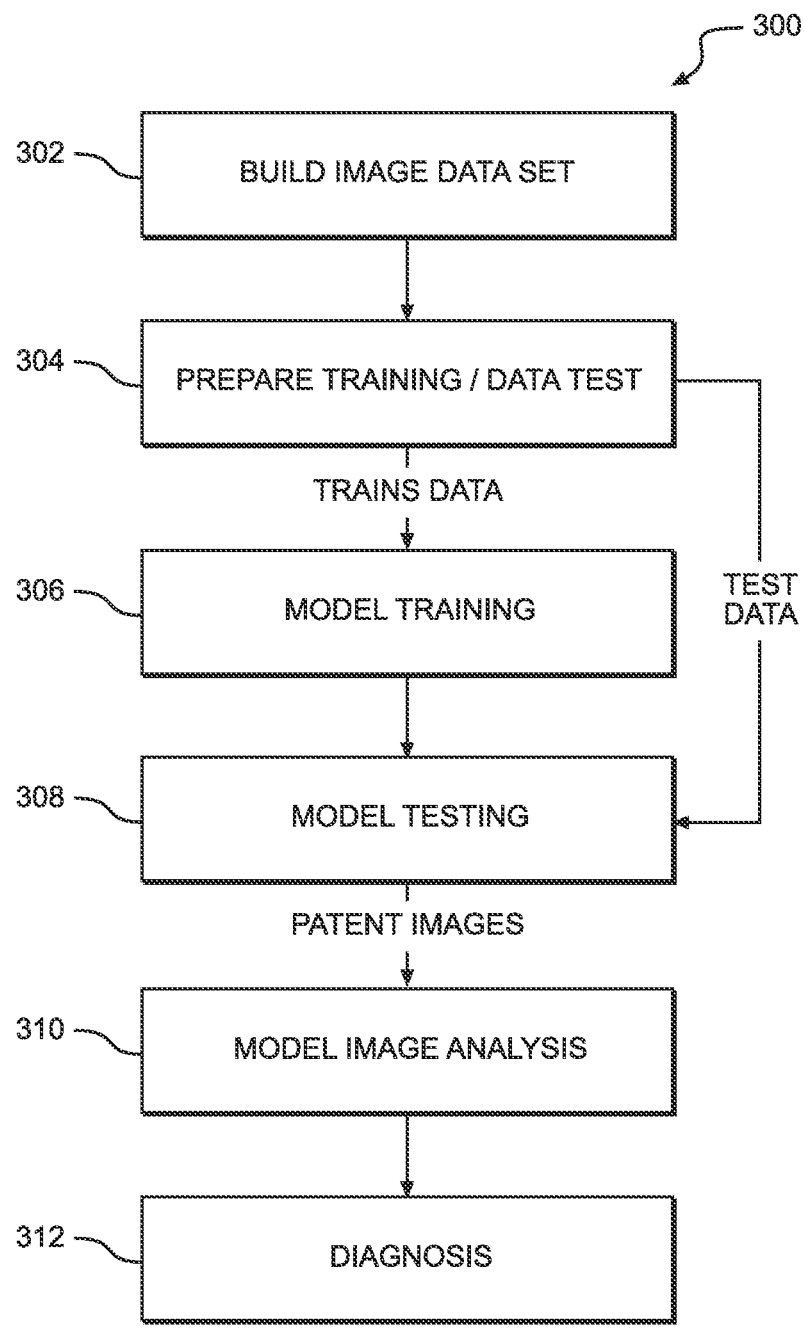
FIG. 3 shows a process flow diagram of generating an ICH volumetric analysis model according to various embodiments.

Referring now to FIG. 3, a method 300 for generating a CNN model for ICH volumetric analysis is shown. With reference to FIGS. 1-2, the computing device 102, may collect or aggregate a number of CT image scans of a patient's cranium, i.e., brain images, and generate a CNN model using a portion of the collected CT images. The CNN model 212 is both trained and tested on tagged/segmented CT images to ensure accuracy. Once the CNN model output error is below an error threshold, it is deployed on incoming CT images of patients with ICH as an input to identify changes to an ICH region that suggest changes to a patient's medical condition.

By way of example, the initial CNN data set, e.g. N=300 patients, may comprise 397 in-patient CT images with a total of 12,968 2D image slices, all of which is stored in image data 210 within memory 202. The training data set is a portion of this initial CNN data set, e.g. n=260 patients, comprising 357 in-patient CT images with 11,556 2D image slices. The test data is the remaining portion of the initial CNN data set, e.g. n=40 patients, comprising 40 in-patient CT images with 1,412 2D image slices. Baseline patient characteristics should be comparable between the training and test cohorts.

Before training of the CNN model 212 can occur, CT images may be converted into Digital Imaging and Communications in Medicine (DICOM) image stacks, each stack having multiple 2D image slices. This may occur at the CT imaging devices 104A-C or at computing device 102. Thus, the conversion of CT image data into DICOM format may occur before or after transmission of the CT imaging data by the CT imaging devices 104A-C to the computing device 102. Thus, the image data 210 used to train the CNN model may be CT image data and/or DICOM image stacks.

The slices of each image stack must be reviewed and tagged, e.g. segmented, to provide the model with labelled data from which it can learn to identify ICH region volumetry. As part of the segmentation process, CT images must first be evaluated for inclusion into a model generation data set. Images collected by the CT imaging devices 104A-C are reviewed by neurological imaging professionals to ensure that collected images meet inclusion criteria for addition to the model generation data set. Thus, the method 300 may begin with the collection, sorting, and segmentation of CT images received from the various CT imaging devices 104A-C.

In block 302, the model generation data set is composed and stored on the computing device 102. That is, the network communication interface 260 may receive CT image data and/or a DICOM image stack associated with CT image data via network 110, or directly from a CT imaging device 104A. The processor 230 may pass the received data to memory 202 for storage as image data 210. A portion of the stored image data 210 is selected for segmentation to form the model generation data set. The model generation data set is made of a portion of the image data 210 and includes CT scans of ICH locations from patients presenting with spontaneous ICH. Some of the CT images obtained from the CT imaging devices 104A-C may be excluded from the model generation data set in order to reduce the presence of non-representative image segments. The CT images excluded from the model generation data set may include those that were obtained (1) after surgical ICH evacuation, (2) more than 14 days after the bleeding event, (3) CT images classified by neurologist or radiologist reviewers as indicating primary IVH and (4) secondary ICH causes such as anticoagulant use, trauma, brain tumor, hemorrhagic transformation of cerebral infarction or vascular abnormality. These aforementioned reasons for exclusion are termed exclusion criteria. To ensure that the exclusion criteria are appropriately identified, CT image metadata may be evaluated by the processor 230. In various embodiments, the metadata for received CT images is stored in the data store in association with the images and is part of the image data 210. Thus, the processor may check for exclusion criteria through a series of queries to the data store, without requiring a review of the actual image files to obtain metadata.

After applying the exclusion criteria, selection of CT images for inclusion in the model generation data set is accomplished by creating patient identifiers for a number of patients having CT scan images. By way of example, CT images of 300 patients may be selected for inclusion in the model generation data set. The number of patients selected for inclusion into the model generation data set may be the same or less than the number of CT images selected for inclusion. This is because each patient may be associated with multiple CT images, and each CT image may have multiple slices. After application of the exclusion criteria, various methods of selection may be used to identify patients for inclusion in the model generation data set. Patients may be selected in a manner that is consecutive, random, alternating, or the like.

In block 304, a user of the computing device 102 prepares the training and test data sets based on the collected CT images. For example, the processor 230 may execute applications 220 to enable segmentation of the CT images within the model generation data set and the separation of the resulting segmented images into testing data and training data sets. Proper image segmentation by human participants is an important part of CNN model generation. Accurate segmentation and identification of ICH regions within each slice of a CT image improves the accuracy of any CNN model trained using the segmented data. Thus, preparation of the data set is important to ensuring the efficacy of CNN model results in informing diagnostic decisions. Preparation of the collected CT images includes separation of the data set into a training set and a test set. Each slice of the CT images is then segmented manually by the user.

To create the training set and the test set, identifiers for the patients whose images were included in the model generation data set may be shuffled in a random or pseudorandom manner and then divided into two groups. The first group, e.g., 40 patient identifiers of the randomly shuffled patient identifiers may be selected for the test group and the CT images corresponding to those patient identifiers are added to the test data set. The patient identifiers remaining in the randomly shuffled patient identifiers, e.g., 260 patient identifiers, are added to the training group and their corresponding CT images added to the training data set. Other techniques for separating the model generation data set into a test set and a training set may be used to generate the two data sets. Further, the number of patient identifiers included in each of the test set and the training set may vary.

In various embodiments, the process of segmenting the images of the data sets may include two phases. The first phase includes the manual segmentation of CT image slices included in the training data set. Manual segmentation may be performed by a single user who is trained in medical imaging analysis or a group of users who are trained in medical imaging analysis arriving at a consensus. These manually tagged and segmented images may be used to generate and train the CNN model. The second phase of image segmentation includes the manual segmentation of CT image slices within the test data set. The second phase of segmentation may be carried out by two or more users who are trained in medical imaging analysis and who did not perform segmentations for the training data set to ensure the accuracy and objectivity of test set image segmentation. The average of the results between the users performing test data set segmentations are the standard by which the CNN is tested against. These second phase results are used to test and validate the trained CNN model's identification of ICH region changes.

In segmentation phase one, the CT images within the training set are manually segmented by one or more users. The ICH region hyperdensity may be manually traced on each 2-dimensional (2D) slice of each 3-dimensional CT image stack using an input device connected to the input/output interface 250. A segmentation software application of applications 220 running on the computing device 102 may include processor-executable instructions to translate input device signals into annotations to the CT image slices. For example, the open-source software platform 3D Slicer 4.8 (National Institutes of Health, Bethesda, MD) or similar CT image slice annotation software may be one of applications 220 and may be used for manual segmentation. Visual inspection and comparison to the contralateral hemisphere by the one or more users, may be used to differentiate ICH from IVH or subarachnoid hemorrhage. The segmented training set is then used to train the CNN model.

In phase two of segmentation, a manual segmentation is performed on the test data set with reference to phase one. This provides a reference set or a ground truth for comparison to the results of executing the CNN model on the test set. To improve reliability of user segmentations, repeat manual segmentations may be performed in a subset of CT scans randomly selected from the test set after a minimal interval of time such as of 7 days since the original segmentation rating.

For the manual segmentation methods in phase one and phase two, the calculation of ICH region size is performed by taking each CT image stack and determining the distance between each volumetric pixel. The distance between each volumetric pixel, which is unique to each CT scan, is transferred from the CT imaging devices 104A-C and stored as metadata saved as image data 210. The number of segmented volumetric pixels ("voxels") within the identified ICH volume is then multiplied by the distance between each voxel in the x, y, and z dimensions. The time required to complete ICH volumetry analysis for each CT image is calculated and stored in the data store. In cases where more than one user performed segmentations on the same CT scan, the ICH region sizes, and the times required to complete ICH volumetry analysis are average across all of the segmenting users to yield mean values.

$$\text{Area} = num_{vox} * x_{depth} * y_{depth} * z_{depth}$$

$$\text{Volume} = \frac{\text{Area}}{1000}$$

In various embodiments, the completion of segmentation phases one and two results in a set of reference images with segmented ICH regions for both the training data set and the test data set. In some embodiments, the segmented CT images may be stored in the data store as a reference training set and a reference test set. In other embodiments, only the segmentation geometry is stored for each CT image slice as a reference. That is, only the values of the segmentation size, border, and density may be stored in association with a CT image slice. In other embodiments, both the annotated CT image slices and the values of the segmentation size, density, and borders may be stored in association with the CT image slice in the data store. For each 3D ICH image stack, the segmentation values of the CT image slices of that stack may be used to calculate an overall volumetry value for the ICH volume presented within the CT image as described above.

III. CNN Model Architecture

Figure 4:
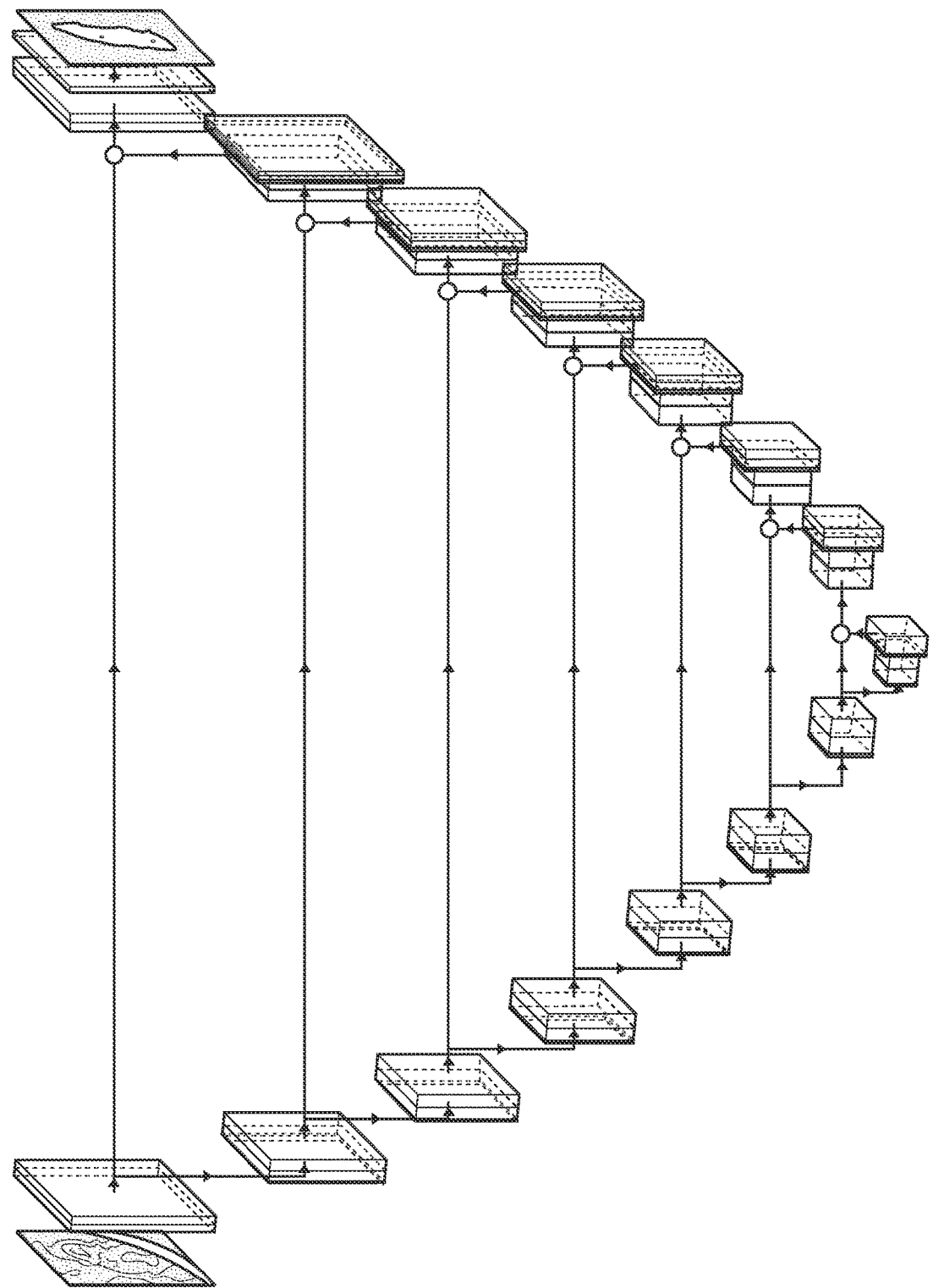
FIG. 4 shows a block diagram of a convolutional neural network for ICH volumetry analysis according to various embodiments.

Referring now to FIG. 4, a CNN model architecture for ICH volumetry analysis according to the various embodiments is shown. With reference to FIGS. 1-3, the computing device 102 builds a CNN model 212 using the training data. The model 212 architecture may be well-suited to medical image processing and the identification of image regions within CT images. Selection of an architecture for the CNN model is important to ensuring that the CNN model 212 accurately identifies changes in ICH volumetry across CT images.

The CNN model 212 is designed to accept inputs of CT image data that has been pre-processed methods of which may follow those detailed in subsequent sections. CT image stacks may be segregated into two-dimensional image slices for input into CNN model 212. Once the image slice has passed through the CNN model 212, the model may generate a two-dimensional binary segmentation of the ICH region. The corresponding CT image identifiers will be used to re-assemble three-dimensional image stacks. In some cases, the CNN model 212 may accept three-dimensional image stacks as the input and generate a three-dimensional segmentation of the ICH region volume. In embodiments in which the CNN model 212 accepts multiple CT image stacks that correspond to a single patient identifier, the resultant segmentation outputs are stored in the data store and changes in the segmentation size, border or density may be used to determine a change in the patient's medical condition.

To further the training data and testing data preparation, each 3D image stack and its corresponding manually segmented ICH region are converted into a feature vector. That is, all pixels included in the 3D image stack of the CT scan and its manually segmented ICH region may be added to a 2, 3, or 4 channel vector, e.g. a NumPy array. The feature vector may be resized to an input matrix of 1×256×256 using bicubic interpolation.

A threshold of 0 to 120 Hounsfield Units (HU) is applied to the original dynamic range. This removes the high-density bone of the skull, retaining the lower density structures that lie within the calvarium. To further constrain the dynamic range, windowing may be performed by applying a HU range of, for example 30 to 120 HU, to the CT image and centering the image at a level of, for example 60 HU. The window enhances brightness and contrast to highlight the ICH and the surrounding soft tissue structures, facilitating delineation of the ICH boundary or border.

After conversion of the pixels of the 3D image stack of the CT scan and its manually segmented ICH region into a feature vector, the range of intensity values of the data representing the 3D image stack of the CT scan are organized to a normal distribution. This is performed by first calculating the mean and standard deviation of HU levels across all CT image stacks included in the model generation data set, for example, across 357 in-patient CT images. For each pixel of each 2D CT image slice, the mean is subtracted. The result is then divided by the standard deviation.

$\mu = \text{mean}(\text{images})$ $\theta = stdev(\text{images})$ $\text{images}_{normal} = (\text{images} - \mu) \div \theta$ Various types of noise may influence the image quality for image processing. These may include impulse noise which makes the intensity of a corrupted pixel much higher or lower than its neighbors, missing image samples which occurs when parts of the image are missing, damaged or partly occluded by undesired objects, damaged images which are caused by degradation due to lost or anomalous pixel values, packet loss which can occur during image transmission and/or tampering of the images. Restoration of the noisy images may be achieved using curvature driven image denoising. The normalized grayscale image channel vectors are contoured using a curvature driven image denoising algorithm. Incorporating the curvature of the image level preserves the edges of the image surface while simultaneously smoothing within the region of pixel noise.

In various embodiments, the CNN model 212 architecture is a contracting and expanding topology, similar to the U-Net convolutional network architecture for image segmentation. The CNN model 212 has a contracting path and an expansive path. The contracting path comprises repeated application of two padded convolutions of a fixed kernel size which defines the field of view of the convolution i.e. 3×3 pixels. The kernel size is selected to balance computational efficiency while preserving complexity of the image analysis technique. Padding adds zero value pixels to the borders of the feature vector to avoid cropping of the image after each convolution. Padding also standardizes the number of times that the convolution is applied to each grayscale pixel, irrespective of the pixel's location within the image. Each convolution is followed by a rectified linear unit (ReLU) and a 2×2 max pooling operation. The max pooling operation calculates the largest value of each field of view in the convolution. A 2×2 filter with a stride of 2 pixels for down sampling is used to simultaneously achieve a gradual reduction in the x and y dimensions of the feature vector, thereby avoiding large scale down sampling and inadvertent loss of relevant image characteristics. At each down sampling, the number of image channels is doubled. The number of image channels represents the depth of the image feature vector i.e. z dimension, whereby each channel responds to a different image characteristic.

Each step in the expansive path comprises an up sampling of the feature vector using a 2×2 filter with a stride of 2 pixels. This is followed by a 2×2 convolution that halves the number of image channels. A concatenation is performed by stacking the feature vector from the expansive path with the corresponding feature vector from the contracting path, thereby linking the two feature vectors. The padded border of the feature vector from the contracting path is cropped as necessary to equalize the x and y dimensions between the two feature vectors. This step is followed by two padded convolutions of the fixed kernel size used for the contracting path, i.e. 3×3 pixels. Each convolution is followed by a ReLU. At the final layer, a convolution of a fixed 1×1 pixel kernel size flattens the three-dimensional feature vector with a depth of, for example, eight channels, into a two-dimensional feature vector with the desired number of classes. In this case, there are two classes, 0 and 1, whereby 1 represents ICH region and 0 represents no ICH region. In total, the CNN model may consist of, for example, 31 convolutional and 7 pooling layers. The number of layers is selected to balance computational efficiency with the complexity of the image analysis technique.

To help the CNN learn complex patterns in the data, non-linear properties are added. The ReLU activation function is used to add these non-linear properties by transforming the summed and weighted input of feature vectors to an output value which is fed into the next layer of the network. The ReLU outputs a small value for small or negative inputs, and a large value if its inputs exceed a threshold. This mimics the physiology of neurons which fire at a certain stimulus threshold.

Batch normalization may be used between each convolution and ReLU layer. The mean and the variance of the feature vector inputs are applied to organize the inputs by a normal distribution. This may reduce the effects of bias and outliers during the activation function, thereby improving efficiency and stability of the CNN.

Regularization methods may be employed, including dropout and L2 regularization. Dropout randomly selects pixels to be removed during training, giving greater weight to the adjacent pixels when making predictions. This reduces the sensitivity of the CNN to the importance of specific pixels and allows multiple independent representations to be learned by the CNN. This, in turn, results in a CNN that is capable of better generalization and is less likely to overfit the training data. Overfitting causes premature convergence to the training data, resulting in poor performance of the CNNs on the testing data, thereby resulting in inaccurate ICH border detection. 50% dropout may be used, which applies the highest possible variance to the normally distributed feature vector inputs. L2 regularization penalizes outlier pixels weighted with very high or very low values by making them close to zero.

The described architecture is particularly well-suited to the fine grain identification of regions of a CT image that indicate changes in ICH volumetry. This CNN model is trained and tested using the feature vectors derived from the segmented training data set and the segmented testing data set.

III. CNN Model Training and Testing

Development of a CNN model requires training the model with a tagged, training data set. The trained model is tested using a second tagged data set, to ascertain the accuracy of the CNN model's predictions. Training of a CNN model may require several rounds of training and refining weights of the model in order to improve accuracy of the CNN model predictions. Various embodiments include the use of the training data set and the test data set, which are used to train and test a CNN model for identifying changes in ICH volumetry within CT images.

In block 306 of method 300, the computing device may build a CNN model for ICH volumetry analysis in CT images. For example, the processor 230 may execute the model building module 214 to build and test a CNN model 212.

To improve spatial invariance, the feature vectors from the training data set may be augmented before they are used as model inputs. Introducing spatial invariance reduces bias and improves the ability of the model to adapt to various types of data acquired in a variety of conditions. For example, in a real-world setting, the model should be able to identify ICH regions in different orientations, without exposure to these specific orientations within the tagged training data set. This may be achieved by applying affine distortions, which include translation, rotation, scaling, and shear, to the feature vectors of the training data set. In living tissue, deformation is a common variation. An additional technique to improve spatial invariance is creation of elastic deformations. A deformation field is created using a matrix sized according to the dimensions of the feature vectors of the training data set. Each element of this matrix is randomly sampled from a Gaussian distribution with a mean of 0 and a standard deviation which represents the elasticity co-efficient. The elasticity co-efficient is set as a scale according to the dimensions of the feature vectors of the training data set, for example 18 pixels. The maximum initial value for the random displacement is also set as a scale according to the dimensions of the feature vectors of the training data set, for example 384 pixels. The displacement of each pixel is then converted to integer values and re-sized to the original feature vector dimensions using bicubic interpolation.

Initial kernel weights were drawn from a Gaussian distribution. A pixel-wise Dice Co-efficient (DC) may be applied to the final feature map for loss function computation. The DC is defined as the similarity between the CNN output and the reference ICH segmentation corresponding to each CT scan input. This is reported on a scale of 0 to 1, with 1 indicating identical segmented volumetric pixels between the CNN output and the reference segmentation.

$$DC = \frac{2xy}{x+y}$$

Where x represents the number of segmented volumetric pixels in the CNN model output and y represents the number of segmented volumetric pixels in the corresponding reference from the training or test data set.

The loss function may be defined as the inverse of the DC.

Loss=1−DC

The loss function may be defined as the error function. Proceeding backwards through the network, the gradient of the error function is calculated, and this is termed back-propagation. The gradient of the error function is then used to update the weights of each kernel before the next forward pass through the CNN. These steps are termed optimization. Adam, derived from adaptive moment estimation, is an optimizer which utilizes Nesterov momentum. It adapts the learning rate for weight updates to both the mean and the variance of the gradient. This may be used to achieve a faster convergence towards the loss function minima than other optimization methods.

The CNN model 212 may be trained for numerous repetitions. For example, the CNN model 212 may be trained for 100 epochs using a batch size of 32 and an initial learning rate of 0.0001. The hyperparameters including the number of repetitions, batch size, dropout and initial learning rate may vary depending on the accuracy desired and the granularity of CT image resolution.

In block 308, the CNN model 212 is tested on CT images from the testing data set. For example, the processor(s) 230 may use the testing module 216 to test the accuracy of the CNN model 212. The trained CNN model 212 is used to generate ICH segmentations from CT scans in the test data set and thereby identify changes in ICH region volumetry. The performance of the CNN model 212 on the testing data set is primarily assessed using the volumetric DC. As defined above, it represents the similarity between the tested and reference ICH segmentations for each CT scan.

Figure 5:
FIG. 5 shows a data table illustrating performance parameters of a test data set according to various embodiments.

Referring to FIG. 5, a data table 500 shows performance of the CNN model 212 using the test data set of the image data 210. Secondary performance parameters for the CNN model 212 include the Hausdorff distance, which measures the maximum distance between two point sets. It is defined as the maximum distance, in mm, between the edges of the tested and reference ICH segmentations for each CT scan in the training data set. It can be used to assess for differences between the edges of two objects that may otherwise have adequate spatial overlap (spatial overlap is measured by the DC). The secondary parameters also include the mean surface distance, which is defined as the mean distance, in mm, between the edges of the tested and reference ICH segmentations for each CT scan in the training data set. Further, the secondary parameters include relative volume difference, which is defined by the equation below:

$$\text{Percent relative volume difference} = \frac{(x_{voxels} - y_{voxels})}{y_{voxels}} \times 100$$

Where x represents the number of segmented voxels (volumetric pixels) in the CNN output and y represents the number of segmented voxels in the reference from the test data set. The secondary parameters further include the mean and median segmented ICH volumes and the mean volumetric analysis time, which is defined as the sum of the number of seconds required to perform volumetric analyses for each scan divided by the total number of scans. Volumetric analysis is defined as the processes of performing ICH region segmentations and subsequent calculations of ICH region volumes from that segmentation.

The table in FIG. 5 compares the performance of the trained CNN model 212 performing fully automated segmentation on the CT images in the test data set, to the reference images segmented using the manual segmentation method. The semi-automated segmentation may, optionally, be performed using a second segmentation software application of the applications 220, such as the Analyze 12.0 software platform (Mayo Clinic, Rochester, MN). First, a temporary limit boundary is drawn manually which approximates the edges of the ICH region hyper density as determined by the user. This may be followed by use of the input device to manually place a seed point to approximate the center of the ICH region as identified using visual inspection by the user. A region-growing Hounsfield Unit (HU) intensity threshold tool, set at 44-100 HU, may then be utilized by the input device for ICH segment selection, centered around the seed point and extending to the edges of the limit boundary. The user may manually adjust the HU threshold range to add or remove segments from the computer-selected region of interest at their discretion.

With the manual segmentation method as the reference standard, the mean volumetric DC, Haussdorf distance, surface distance, and relative volume difference for the fully automated segmentation algorithm may be 0.894±0.264, 218.84±335.83 mm, 5.19±23.65 mm, and 17.96±14.55%, respectively. In embodiments that utilize the semi-automated segmentation method as the reference standard, the mean volumetric DC, Haussdorf distance, surface distance, and relative volume difference may be 0.905±0.254, 277.69±368.04 mm, 5.09±16.47 mm, and 16.18±14.18%, respectively.

Referring now to FIG. 6, there are shown exemplary CT images with ICH regions segmented according to various segmentation methods. With reference to FIGS. 1-6, the CT images of the test data set may be segmented using manual, semi-automated, and fully automated ICH segmentation methods. Example results of ICH segmentation methods applied to CT images in the test data set are shown in different columns. Column A includes the original CT image slice to which segmentation methods are later applied. Column B includes the manual ICH segmentation results for the corresponding image in Column A. That is, the images appearing in column B are the result of applying manual segmentation methods to the CT image appearing in the same row of column A. Column C includes the results of applying semi-automated segmentation methods to the corresponding CT image in column A, in embodiments in which semi-automated segmentation is used. Column D includes the results of applying the fully automated segmentation (CNN model 212) to the corresponding CT image of column A. A ventricular catheter is visualized in the second row of images. Thus, the CT images of FIG. 6 provide visual comparison of the results of the CNN model 212 to the reference segmented CT images of the test data set.

Referring now to FIGS. 7 and 8, there are shown data tables comparing ICH volume and analyses times across segmentation methods applied to CT images of the test data set. In the test data set, the mean segmented ICH volumes are 25.73±23.72, 26.54±25.24, and 25.60±25.99 mL using the manual (optionally, the semi-automated) and fully automated ICH segmentation methods, respectively and this difference may not be significant (p=0.915).

In the test dataset, the mean volumetric analysis times are shown as 201.45±92.22, 288.58±160.32, and 11.97±2.70 s/scan for the manual, semi-automated and fully automated ICH segmentation methods, respectively. There may be a significant difference in volumetric analysis times among the three segmentation methods (P<0.0001). Fully automated segmentation is shown to be significantly faster than manual (mean difference=−189.48 [−246.17 to −132.79] s/scan) segmentation methods. The combination of similarity between segmented ICH volumes between those produced by the manual and CNN model 212 and the faster processing of ICH volumetry by the CNN model 212 drastically reduces the amount of time needed to identify changes in ICH volumes in patients. The CNN model 212 is designed as an image analysis tool. Therefore, testing for similarity between segmented ICH images (i.e. DC, Hausdorff distance, mean surface distance and relative volume difference) estimates the CNN model 212 accuracy. However, the practical usefulness of CNN model 212 to detect ICH volume changes, is established by testing for similarity or lack of significant difference between ICH region volumes measured between manual clinician raters and the CNN model 212. When there is sufficient confidence in the CNN model 212 to identify changes in ICH region volumes without significant difference to the manual clinician raters but with significantly increased efficiency, the CNN model 212 may be deployed on real world CT image data of patients with ICH. This may lead to more rapid diagnosis of volume changes and enable speedier application of life-saving interventions.

Figure 9B:
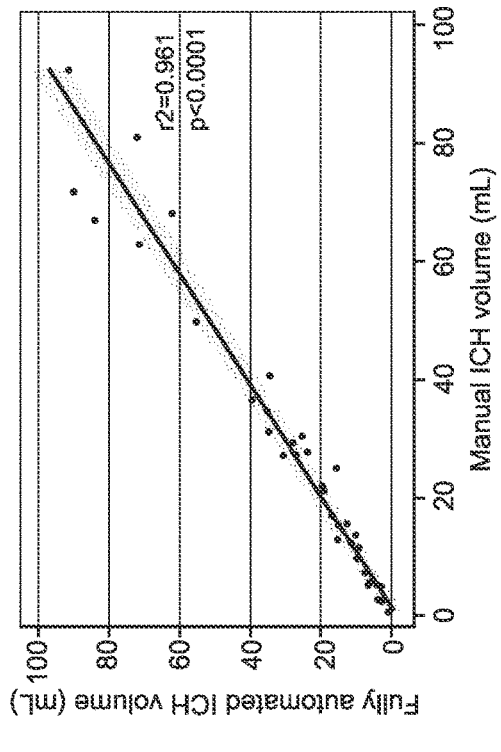
FIG. 9B also shows scatter plot diagrams of ICH volume analyses across segmentation methods according to the various embodiments.
Figure 9D:
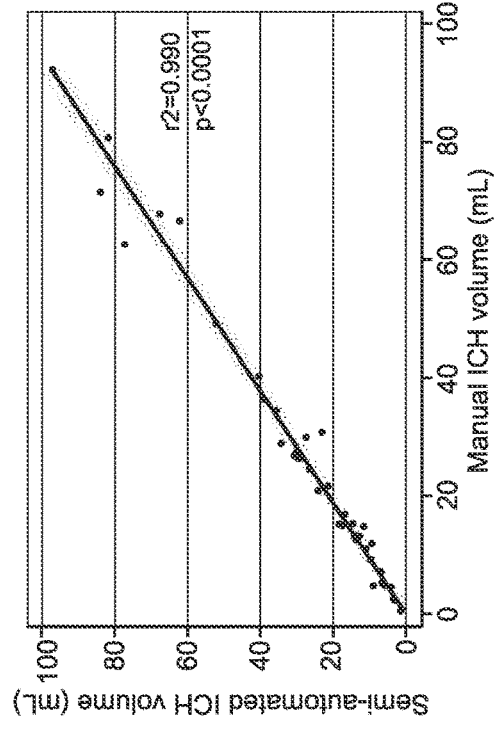
FIG. 9D also shows scatter plot diagrams of ICH volume analyses across segmentation methods according to the various embodiments.
Figure 9A:
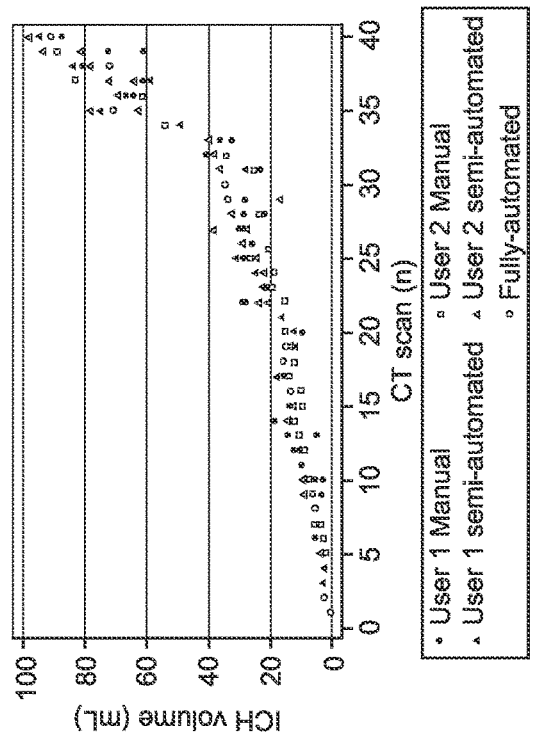
FIG. 9A shows scatter plot diagrams of ICH volume analyses across segmentation methods according to the various embodiments.
Figure 9C:
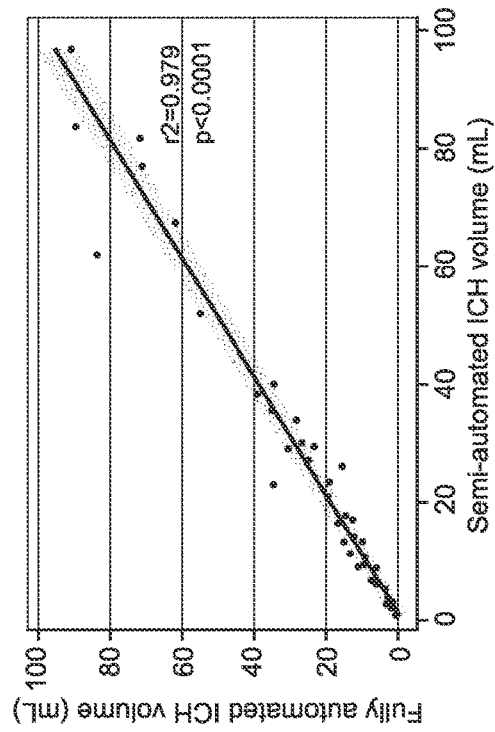
FIG. 9C also shows scatter plot diagrams of ICH volume analyses across segmentation methods according to the various embodiments.

Referring to FIGS. 9A-D, scatter plots are shown for each of the CT image segmentation methods. With reference to FIGS. 1-9D, the performance of various CT image segmentation methods is plotted for the users who performed manual (and optionally, semi-automated) segmentation. Scatter plots A-D compare segmented ICH regions across segmentation methods. FIG. 9A shows a comparison of the segmented ICH volumes prepared by each user, applying manual, (optionally semi-automated) and fully automated (CNN model 212) segmentation methods to CT images of the test data set. FIG. 9B shows a comparison of mean segmented ICH volumes among both users resulting from the application of fully automated vs manual segmentation to the CT images of the test data set. FIG. 9C shows a comparison of mean segmented ICH volumes among both users resulting from the application to the CT images of the test data set. FIG. 9D shows a comparison of mean segmented ICH volumes among both users resulting from the application of semi-automated vs manual segmentation to the CT images of the test data set. Strong correlations may be observed between fully automated versus manual ($R2$=0.981 [0.960–0.990], P<0.0001; FIG. 9B), fully automated versus semi-automated ($R2$=0.978 [0.960–0.989], P<0.0001; FIG. 9C), and semi-automated versus manual ($R2$=0.990 [0.985–0.996], P<0001; FIG. 9D) segmentation methods.

Figure 10A:
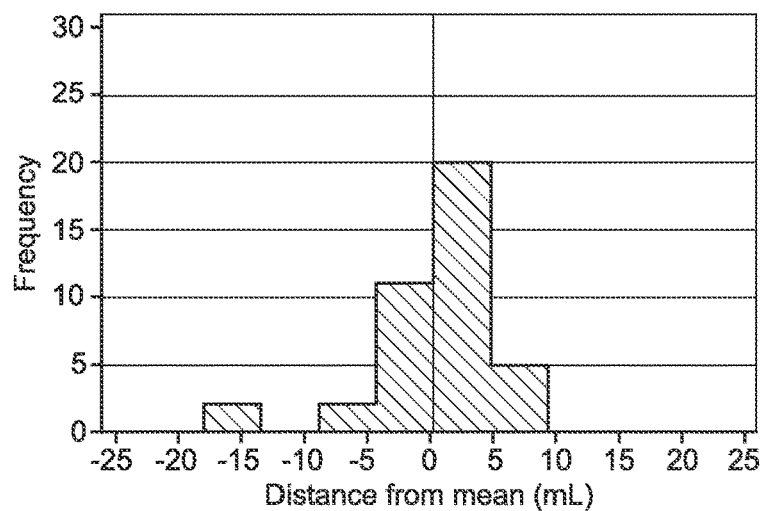
FIG. 10A shows histogram plots of differences in ICH volumes across segmentation methods according to various embodiments.
Figure 10B:
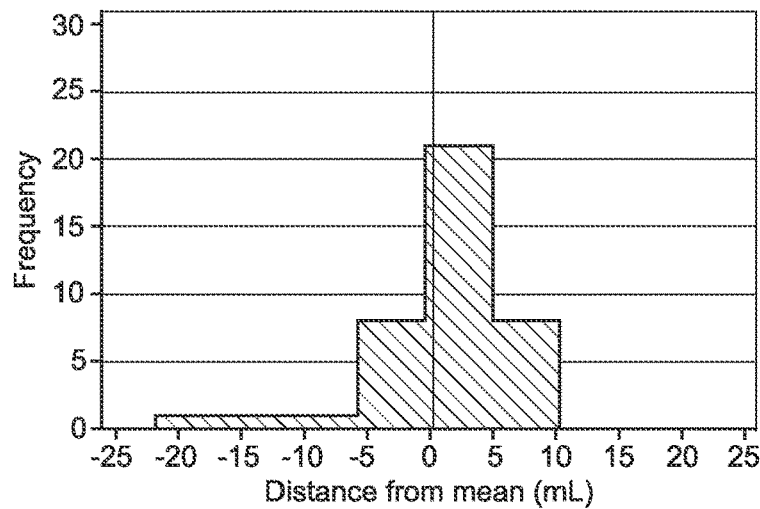
FIG. 10B shows histogram plots of differences in ICH volumes across segmentation methods according to various embodiments.
Figure 10C:
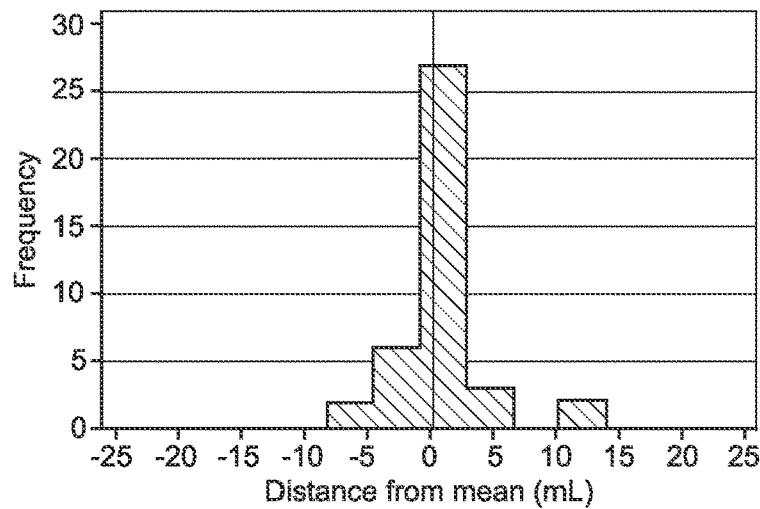
FIG. 10C shows histogram plots of differences in ICH volumes across segmentation methods according to various embodiments.

Referring now to FIGS. 10A-C, there are histogram charts showing the differences in segmented ICH volumes across segmentation methods. With reference to FIGS. 1-10C, plotted differences in segmented ICH volumes for each CT image are shown for each applied segmentation method. In FIG. 10A, the differences between the resulting segmented ICH volumes from fully automated versus manual segmentation methods is shown. FIG. 10B shows the differences between the resulting segmented ICH volumes from fully automated versus semi-automated segmentation methods applied to the CT images of the test data set. FIG. 10C shows the differences between the resulting segmented ICH volumes from manual versus semi-automated segmentation methods applied to the CT images of the test data set IV. Diagnostic Improvements In block 310 of FIG. 3, the processor 230 may utilize the CNN model to perform CT image analysis on one or more CT images of a patient. For example, the processor 230 may pass received CT images to the CNN model 212 as the input to obtain an estimate of ICH volumetry changes. Various embodiments include the use of the trained and tested CNN model 212 to identify and diagnoses changes in ICH volume in patients. The computing device 102 may receive patient CT images from one or more CT imaging devices 104A-C, throughout the lifecycle of patient care. The computing device 102 may receive these CT images and store them in image data 210 along with a patient identifier. The slices of the CT image may be converted into feature vectors, which are passed as inputs to the CNN model 212.

In block 312 of FIG. 3, the processor 230 may use the output of the CNN model 212 to identify changes in ICH volumetry and diagnose the significance of these changes. For example, the processor 230 may execute diagnostic module 218 to compare or otherwise analyze the output of the CNN model 212 executing on the feature vectors of the received patient CT images. The results of the CNN model may be an output that enables diagnosis of ICH volumetry changes, e.g. shape, size, density, etc. This may be the use of diagnostic module 218 to compare CNN model results across individual 2D CT image slices or 3D CT image stacks for a patient. Alternatively, the diagnostic module 218 may use the direct output of the CNN model as a measurement of difference or change.

In some embodiments, the difference, whether calculated or directly obtained from the CNN model, may be compared to one or more thresholds to determine if the volumetry of the ICH region has grown or subsided significantly. Based on the results of this comparison, the ICH region is diagnosed as either growing or shrinking. That is, if the difference exceeds an upper threshold, then the ICH region may be said to be growing. However, if the difference is below a lower threshold, the ICH region may be said to be shrinking. Differences may be stored along with the image data or tracked in a patient database elsewhere in the network environment 100. If the ICH region is said to be growing, this information may be used to implement various treatments for the patient including surgery, medicines or the like. If the ICH region is said to be shrinking, this may be used to characterize a success in treatment. Diagnoses of ICH region changes may also be used in medical research efforts to study their effects on patient outcomes. For example, if the ICH region is said to be changing, this information may be stored in a patient database elsewhere in the network environment to analyze differences in patient characteristics such as medical history, laboratory studies or genetic markers and/or differences in long term neurological impairment or survival between patients with or without these ICH region changes (i.e. shape, size, density, growth, shrinkage).

The above-described embodiments provide solutions to rapid ICH volumetry analysis challenges using a CNN model trained on CT images of patients known to have ICH. By enabling the identification and visualization of ICH volumetry changes, the various embodiments may improve the efficiency and standardization of hematoma change diagnosis. By improving the speed of ICH volumetry changes with no loss of accuracy, the various embodiments improve the speed with which life-saving interventions may be applied to patients. They also reduce the measurement error between different humans performing the same task, thereby improving the precision of these measurements.

It is to be understood that the above description is intended to be illustrative, and not restrictive. Many other implementations are apparent upon reading and understanding the above description. The scope of the disclosure should, therefore, be determined with reference to the appended claims, along with the full scope of equivalents to which such claims are entitled.

In the above description, numerous details are set forth. It is apparent, however, that the disclosure may be practiced without these specific details. In some instances, structures and devices are shown in block diagram form, rather than in detail, in order to avoid obscuring the disclosure.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "determining", "identifying", "updating", "copying", "publishing", "selecting", "utilizing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems appears as set forth in the description below. In addition, the disclosure is not described with reference to any particular programming language. It is appreciated that a variety of programming languages may be used to implement the teachings of the disclosure as described herein.

The disclosure may be provided as a computer program product, or software, that may include a machine-readable medium having stored thereon instructions, which may be used to program a computer system (or other electronic devices) to perform a process according to the disclosure. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., carrier waves, infrared signals, digital signals, etc.)), etc.

It is to be understood that the above description is intended to be illustrative, and not restrictive. Many other implementation examples are apparent upon reading and understanding the above description. Although the disclosure describes specific examples, it is recognized that the systems and methods of the disclosure are not limited to the examples described herein, but may be practiced with modifications within the scope of the appended claims. Accordingly, the specification and drawings are to be regarded in an illustrative sense rather than in a restrictive sense. The scope of the disclosure should, therefore, be determined with reference to the appended claims, along with the full scope of equivalents to which such claims are entitled.

What is claimed is:

1. A computing device for intracerebral hematoma analysis comprising:
    a processor;
    a network communication interface;
    a memory in communication with the processor and having stored thereon, processor-executable instructions for causing the processor to perform operations comprising:
        receiving, from a computerized tomography (CT) imaging device, a three-dimensional CT image of a patient exhibiting ICH;
        converting the three-dimensional CT image into two-dimensional CT image slices;
        converting each CT image slice into a feature vector;
        passing the feature vectors to a convolutional neural network (CNN) model as input;
        executing the CNN model using the feature vectors of the two-dimensional CT image slices to determine a boundary of the ICH and to obtain an estimate of change in absolute ICH volumetry; and
        based on the estimate of change in the absolute ICH volumetry, determining a change in the medical status of the patient's ICH volume according to whether the absolute ICH volume is expanding or shrinking.

2. The computing device of claim 1, wherein determining a change in the medical status of the patient's ICH volume further comprises:
    comparing the estimate obtained from the CNN model to a threshold; and
    based on the results of the comparison, determining a change in the medical status of the patient's ICH volume.

3. The computing device of claim 2, wherein the memory has stored thereon, instructions for causing the processor to execute operations further comprising:
    determining a treatment plan for the patient based, at least in part, on the change in the medical status of the patient's ICH volume.

4. The computing device of claim 1, wherein executing the CNN model to obtain an estimate of ICH volumetry is performed for each CT image slice of the CT image; and
    wherein determining a change in the medical status of the patient's ICH volume further comprises:
        comparing the estimate obtained from the CNN model for each CT image slice to a threshold; and
        based on the results of the comparison, determining a change in the medical status of the patient's ICH volume.

5. The computing device of claim 4, wherein the memory has stored thereon, instructions for causing the processor to execute operations further comprising:
    determining a treatment plan for the patient based, at least in part, on the change in the medical status of the patient's ICH volume.

6. The computing device of claim 1, wherein the CNN was trained on a set of manually segmented CT images including ICH.

7. A computing device for intracerebral hematoma analysis comprising:
    a processor;
    a network communication interface;
    a memory in communication with the processor and having stored thereon, processor-executable instructions for causing the processor to perform operations comprising:
        receiving, from a computerized tomography (CT) imaging device, a three-dimensional CT image of a patient exhibiting ICH;
        converting the three-dimensional CT image into two-dimensional CT image slices;
        converting the CT image into a feature vector;
        passing the feature vector to a convolutional neural network (CNN) model as input;
        executing the CNN model using the feature vectors of the two-dimensional CT image slices to determine a boundary of the ICH and to obtain an estimate of change in absolute ICH volumetry; and
        based on the estimate of change in the absolute ICH volumetry, determining a change in the medical status of the patient's ICH volume according to whether the absolute ICH volume is expanding or shrinking.

8. The computing device of claim 7, wherein executing the CNN model to obtain an estimate of ICH volumetry is performed for each CT image slice of the CT image; and
    wherein determining a change in the medical status of the patient's ICH volume further comprises:
        comparing the estimate obtained from the CNN model for each CT image slice to a threshold; and
        based on the results of the comparison, determining a change in the medical status of the patient's ICH volume.

9. The computing device of claim 8, wherein the memory has stored thereon, instructions for causing the processor to execute operations further comprising:
  determining a treatment plan for the patient based, at least in part, on the change in the medical status of the patient's ICH volume.

10. The computing device of claim 7, wherein the CNN was trained on a set of manually segmented CT images including ICH.

11. A method of intracerebral hematoma analysis comprising receiving, via a network communication interface of a computing device, from a computerized tomography (CT) imaging device, a three-dimensional CT image of a patient exhibiting ICH;
  converting the three-dimensional CT image into two-dimensional CT image slices;
  converting, via a processor of the computing device, each CT image slice into a feature vector;
  passing the feature vectors to a convolutional neural network (CNN) model as input;
  executing the CNN model using the feature vectors of the two-dimensional CT image slices to determine a boundary of the ICH and to obtain an estimate of change in absolute ICH volumetry; and
  based on the estimate of change in the absolute ICH volumetry, determining a change in the medical status of the patient's ICH volume according to whether the absolute ICH volume is expanding or shrinking.

12. The method of claim 11, wherein determining a change in the medical status of the patient's ICH volume further comprises:
  comparing the estimate obtained from the CNN model to a threshold; and
  based on the results of the comparison, determining a change in the medical status of the patient's ICH volume.

13. The method of claim 12, further comprising:
  determining a treatment plan for the patient based, at least in part, on the change in the medical status of the patient's ICH volume.

14. The method of claim 12, wherein executing the CNN model to obtain an estimate of ICH volumetry is performed for each CT image slice of the CT image; and
  wherein determining a change in the medical status of the patient's ICH volume further comprises:
  comparing the estimate obtained from the CNN model for each CT image slice to a threshold; and
  based on the results of the comparison, determining a change in the medical status of the patient's ICH volume.

15. The method of claim 14, further comprising:
  determining a treatment plan for the patient based, at least in part, on the change in the medical status of the patient's ICH volume.

16. The method of claim 11, wherein the CNN was trained on a set of manually segmented CT images including ICH.

17. The method of claim 11, further comprising applying a threshold of 0 to 120 Hounsfield Units to the three-dimensional CT image to highlight the ICH.

* * * * *